(12) United States Patent
Eagles et al.

(10) Patent No.: US 6,476,214 B1
(45) Date of Patent: Nov. 5, 2002

(54) INHIBITION OF CYTOKINE PRODUCTION

(75) Inventors: Peter Anthony Minter Eagles, Bromley (GB); Richard Qihao Zheng, London (GB)

(73) Assignee: BTG International Limited, London (GB)

(*) Notice: Subject to any disclaimer, the term of this patent is extended or adjusted under 35 U.S.C. 154(b) by 0 days.

(21) Appl. No.: 09/617,548

(22) Filed: Jul. 14, 2000

Related U.S. Application Data (63) Continuation of application No. PCT/GB99/00179, filed on Jan. 20, 1999.

(30) Foreign Application Priority Data

Jan. 22, 1998 (GB) ............................................... 9801391
Nov. 11, 1998 (GB) ............................................... 9824794

(51) Int. Cl.$^7$ .......................... C07H 21/04; C12N 15/63; C12N 15/00; A61K 9/127
(52) U.S. Cl. .................. 536/24.1; 435/320.1; 435/69.1; 435/69.5; 424/450
(58) Field of Search .................. 435/69.1, 5, 320.1; 514/44; 424/450; 536/24.1

(56) References Cited

U.S. PATENT DOCUMENTS 5,665,591 A  9/1997  Sonenshein et al. ........ 435/375

FOREIGN PATENT DOCUMENTS

| WO | WO 92/18522 | 10/1992 |
| WO | WO 95/08001 | 3/1995 |
| WO | WO 97/41232 | 11/1997 |
| WO | WO 98/51344 | 11/1998 |
| WO | WO 99/23208 | 5/1999 |

OTHER PUBLICATIONS

Haudek et al. Immunogenics 1998; 48:202–207.*
Templeton et al. Nat Biotechnol Jul. 1997; 15:647–52.*
Verma et al. Nat. Sep. 1997; 389:239–242.*
Eck et al. Phar Basis Ther 1995; 77–101.*
Staynov, D. Z. et al., A regulatory element in the promoter of the human granulocyte–macrophage colony–stimulating factory gene that has related sequences in other T–cell–expressed cytokine genes, *Proc. Natl, Acad. Sci. USA* 92, 3606–3610 (1995).
Bielinska, A. et al., Regulation of Gene Expression with Double–Stranded Phosphorothioate Oligonucleotides, *Science* 250, 997–1000 (1990).

(List continued on next page.)

*Primary Examiner*—James Ketter
*Assistant Examiner*—Janice Li
(74) *Attorney, Agent, or Firm*—Nixon & Vanderhye

(57) ABSTRACT

The invention provides a ds-DNA oligomer which has from 25 to 150 base pairs, preferably 25 to 50 base pairs, and comprises the palindrome-containing sequence (one strand only shown) of formula (1):

$$5'B^1 \ldots xN \ldots B^23' \qquad (1)$$

wherein $B^1$ is $_{tgg}$ or $_{ccaa}$ and $B^2$ is correspondingly $_{ccaa}$ or $_{tgg}$ and xN represents from 1 to 30 native nucleotides of substantially the native promoter sequence, together with the complementary strand, the oligomer being modified to make it resistant to degradation and denaturing in vivo. This oligomer or a vector carrying the palindrome-containing sequence (but not necessarily with the modification and not limited by any upper limit on the length of the oligomer sequence) can be used to inhibit transcription of the cytokine gene in vivo and is therefore useful in the therapy of diseases associated with undesired or excess production of cytokine.

7 Claims, 4 Drawing Sheets

OTHER PUBLICATIONS

Cousins, D. J. et al., Regulation of Cytokine Genes Implicated in Asthma and Atopy, *Genetics of Asthma and Atopy* 33, 138–152 (1996).

Staynov, D. Z. et al., A Conserved Motif in the Promoters of Several Cytokines Expressed by Human Th2–Type Lymphocytes, *Int. Arch Allergy Immunol* 107, 217–219 (1995).

Foster, P. S. et al., Interleukin 5 Deficiency Abolishes Eosinophilia, Airways Hyperreactivity, and Lung Damage in a Mouse Asthma Model, *J. Exp. Med.* 183, 195–201 (1996).

Lewis, J. G et al., A serum–resistant cytofectin for cellular delivery of antisense oligodeoxynucleotides and plasmid DNA, *Proc. Natl. Acad. Sci. USA* 93, 3176–3181 (1996).

Gruart–Gouilleux, V. et al., Characterization of the human interleukin–5 gene promoter: involvement of octamer binding sites in the gene promoter activity, *Eur. J. Immunol.* 25, 1431–1435 (1995).

Penix, L. et al., Two Essential Regulatory Elements in the Human Interferon γ Promoter Confer Activation Specific Expression in T Cells, *The Journal of Experimental Medicine* 178, 1483–1496 (1993).

Gray, P. W. et al., Structure of the human immune interferon gene, *Nature* 298, 859–862 (1982).

Fujita T. et al., Structure of the human interleukin 2 gene, *Proc. Natl. Acad. Sci. USA* 80, 7437–7441 (1983).

Arai, N. et al., Complete Nucleotide Sequence of the Chromosomal Gene for Human IL–4 and its Expression, *The Journal of Immunology* 142, 274–282 (1989).

Tanabe T. et al., Molecular Cloning and Structure of the Human Interleukin–5 Gene, *The Journal of Biological Chemistry* 262, 16580–16584 (1987).

Yasukawa K. et al., Structure and expression of human B cell stimulatory factor–2 (BSF/IL–6) gene, *The EMBO Journal* 6, 2939–2945 (1987).

Mukaida N. et al., Genomic Structure of the Human Monocyte–Derived Neutrophil Chemotactic Factor IL–8, *The Journal of Immunology* 143, 1366–1371 (1989).

Rumbyrt J. S. et al., Characterization and sequence analysis of the human IL–10 promoter, *Genbank Submission u06844* (1994).

McKenzie, A. N. J. et al., Structural Comparison and Chromosomal Localization of the Human and Moulse IL–13 Genes, *The Journal of Immunology* 150, 5436–5444 (1993).

Miyatake, S. et al., Structure of the chromosomal gene for granulocyte–macrophage colony stimulating factor: comparison of the mouse and human genes, *The EMBO Journal* 4, 2561–2568 (1985).

Takashiba, S. et al., Cloning and characterization of human TNFα promoter region, *Gene* 131, 307–308 (1993).

Schwenger, G. T. F. et al., Identification of two novel palindromic regulatory elements in the murine interleukin–5 promoter, *Molecular Immunology* 35, 149–158 (1998).

Karlen, S. et al., How is expression of the interleukin–5 gene regulated?, *Immunology and Cell Biology* 74, 218–223 (1996).

Karlen, S. et al., Two Pathways Can Activate the Interleukin–5 Gene and Induce Binding to the Conserved Lymphokine Element 0, *Blood* 88, 211–221 (1996).

Fiorentini, P. et al., Characterization of a Distal 5'–Flanking Region (–2010/–630) of Human GM–CSF*, *Biochemical and Biophysical Research Communications* 214, 1015–1022 (1995).

Okamoto, T. et al., Regulation of NF–κB and Disease Control: Identification of a Novel Serine Kinase and Thioredoxin as Effectors for Signal Transduction Pathway for NF–κB Activation, *Current Topics in Cellular Regulation* 35, 149–161 (1997).

Aust, G. et al., Differential regulation of granulocyte–macrophage colony–stimulating factor mRNA and protein expression in human thyrocytes and thyroid–derived fibroblasts by interleukin–1α and tumour necrosis factor–α, *Journal of Endocrinology* 151, 277–285 (1996).

Kotsimbos, T. C. et al., Interleukin–13 and Interleukin–4 are Coexpressed in Atopic Asthma, *Proceedings of the Association of American Physicians* 108, 368–373 (1996).

Kishimoto T. T. et al., Gp130 and the Interleukin–6 family of cytokines, *Annu. Rev. Immunol.* 15, 797–819 (1997), Abstract only.

Biasucci, L. M. et al., Elevated Levels of Interleukin–6 in Unstable Angina, *Circulation* 94, Abstract (1996).

Okada, S. et al., Elevated Serum Interleukin–6 Levels in Patients with Pancreatic Cancer, *Japanese Journal of Clinical Oncology* 28, 12–15 (1998).

Baggiolini, M. et al., Human Chemokines: an update, *Annu. Rev. Immunol.* 15, 675–705 (1997), Abstract only.

Klava, A. et al., Interleukin–10. A Role in the Development of Postoperative Immunosuppression, *Archives of Surgery* 132, 425–429 (1997) Abstract only.

Monoclonal Anti–Human Interleukin–10 (IL–10), *Sigma Product Information Sheet* I7392, Abstract (1997).

Glaser, V., Anti–inflammatory inflames Centocor's profits, *Nature Biotechnology* 16, 900 (1998).

* cited by examiner

INHIBITION OF CYTOKINE PRODUCTION

This is a continuation of PCT application PCT/GB99/00179, filed Jan. 20, 1999, the entire content of which is hereby incorporated by reference in this application.

BACKGROUND OF THE INVENTION

1. Field of the Invention

This invention relates to inhibiting the production of cytokines in cells of the body, and thus to the treatment or prevention of diseases associated with excessive production of cytokines. Of especial interest is the production of interleukin-5, a cytokine which is implicated in inflammation of the pulmonary airways, especially in asthma; and TNF-α, a cytokine shown to play a very important role in rheumatoid arthritis.

2. Description of the Related Art

There is now evidence that interleukin-5 (IL-5) plays an important role in the pathogenesis of asthma (Corrigan, Clin. Exp. Allergy 25, 485–487 (1995)). IL-5 is one of the commonest cytokines which are produced by T-helper cells. It is particularly implicated in control of eosinophil functions, including selective chemotaxis, growth differentiation, proliferation, release of cytotoxic proteins and the survival of these cells (Takatsu et al., Adv. in Immunol. 57, 145–190 (1995)). IL-5 also enhances T-cell adhesion to vascular endothelial cells. IL-5 has been detected at the site of the allergic inflammation and in the peripheral blood of patients, its level correlating to the extent of eosinophilia, the severity, and the response of the treatment of asthma (H. Okudaira et al., Int. Arch. Allergy Immunol. 107, 255–258 (1995); Corrigan, Clin. Exp. Allergy 25, 485–487 (1995)). Animal models from murine to monkey have demonstrated the involvement of IL-5 in asthma and the beneficial effects due to the inhibition of the cytokine.

A prophylactic and therapeutic effect of an anti-IL-5 monoclonal, TRFK-5, in a mouse model of allergic pulmonary inflammation has recently been demonstrated (T. T. Kung et al., American Journal of Respiratory Cell and Molecular Biology 13, 360–365 (1995)). The number of eosinophils in the bronchoaveolar lavage (BAL) fluid and lung tissue was reduced and the decrease in bone marrow eosinophils was prevented. Both these effects were being seen to occur in a dose-dependent fashion. After the neutralisation of IL-5, the ovalbumin-allergic mice showed no evidence of increased epithelial damage, oedema, or the presence of mucus that could have resulted from eosinophil apoptosis and release of toxic proteins. In IL-5"knock-out" mice, the airway pathology was abolished (P. S. Foster et al., J. Exp. Med. 183, 195–201 (1996)).

Other groups have worked on guinea pig models and have reported that in studies using anti-IL-5 antibodies, a total inhibition of the development of bronchohyperreactivity to histamine and arecoline after ovalbumin challenge (A. J. M. Van Oosterhout et al., American Review of Respiratory Disease 147, 548–552 (1993)). The number of eosinophils was markedly reduced and the number of neutrophils was not affected, verifying the specificity of IL-5 on eosinophils in asthma. However, antibody therapy in humans has many well-known problems.

An alternative idea which could be contemplated is to inhibit production of IL-5 prior to RNA transcription using a modified synthesised double stranded (msds) DNA sequence to which is similar or identical to a particular part of the promoter region of IL-5, for example the part which binds to a transcription factor.

As a general principle, a DNA "decoy" would be provided which would compete with the native gene for a limited supply of transcription factor. This would be a double-stranded (ds) DNA oligomer modified to prevent it from being destroyed by endogenous DNases. For example, the phosphate linkages could be replaced to a large extent by phosphorothioate linkages. See Bieliaska et al., Science 250, 997–1000 (1990), in relation to interleukin-2.

NOMENCLATURE NOTE

All 5'-non-coding region nucleotide nomenclature used in this patent specification is based on the first nucleotide of the start of the coding region (A of the ATG) being +1 and the nucleotide preceding it −1. All nomenclature used in references has been converted to this basis.

V. Gruart-Gouilleux et al., Eur. J. Immunol 25, 1431–1435 (1995) studied the transcriptional activity of the human IL-5 gene promoter region in mouse EL4 cells, using a series of deletion constructs linked to a luciferase reporter gene. They found that deletions of nucleotides between −358 and −274 or −124 to −79 inhibited the induction of IL-5 promoter activity. Investigation of the −358 to −274 region revealed that the octamer-binding motif 5'-atgcaaat-3' at −290 to −283 was required for full transcriptional activity. See nomenclature note above. Very minor errors of numbering in this paper have also been corrected, taking the sequence of oligo probes as correct.

At about the same time D. Z. Staynov et al., Proc. Natl. Acad. Sci. USA 92, 3606–3610 (1995) and Int. Arch. Allergy Immunol. 107, 217–219 (1995) described a regulatory element in the promoter of the human granulocyte-macrophage colony-stimulating factor (hGMCSF) gene that has related sequences in the gene promoters of human interleukins (hIL-2, hIL-4, hIL-5, hIL-13). The authors identified a palindrome-containing sequence as involved in a DNA-protein interaction, by using nuclear extract from Jurkat cells as the source of protein. A 40 bp sequence of hGMCSF promoter DNA containing cttgg . . . (22N) . . . ccaag "outer" palindromic sequences near each end and a 12 bp-long "inner", AT-rich, palindrome in the centre was found to bind to the nuclear extract by a gel retardation assay (in which the protein-DNA complex migrates more slowly than the DNA alone on a gel). Some of the binding was ascribed exclusively to the outer palindrome and some to the inner. However, the use of these crude nuclear extracts calls into question which proteins were bound. Noting that the outer palindrome motif or a shorter version, ttgg . . . ccaa, is present in the promoters of certain interleukins, the authors speculated that some of the interacting proteins may be gene-specific. As regards IL-5, the conterpart palindrome-containing sequence occurs at nucleotides −514 to −504. However, V. Gruart-Gouilleux et al., above, reported that a deletion of nucleotides −552 to −449 (thus encompassing the whole of Staynov et al.'s palindrome-containing sequence) had little effect on induction of IL-5 promoter activity.

SUMMARY OF THE INVENTION

It has now surprisingly been found that a double-stranded oligomeric deoxyribonucleotide (oligo-DNA), modified to make it resistant to degradation, containing a similar palindrome in hIL-5, inhibits production of hIL-5 in T-cells, apparently by competing with hIL-5 for a transcription factor. It has further been found that there are palindrome-containing sequences comprising the ttgg . . . ccaa motif in the gene promoter region of other cytokines besides those mentioned by Staynov et al., such as TNF-α. These are also inhibitors of transcription of the specific cytokines. The inhibition referred to herein comprises partial or complete prevention of the transcription.

By delivering these oligonucleotides to cells, it will be possible to treat diseases characterised by over-expression of a target gene, leading to unwanted effects at the cellular level, at the level of tissue or organ function and/or throughout the body. These include but are not limited to allergy, asthma, chronic obstructive airways disease or conditions characterised as being inflammation, including autoimmune diseases, or cancer.

In one aspect, the present invention provides a ds-DNA oligomer which has from 25 to 150 base pairs, preferably 25 to 60 and more preferably 50 base pairs, and comprises (i.e. consists of or includes) the palindrome-containing sequence (one strand only shown) of formula 1:

$$5'B^1\ldots xN \ldots B^23' \qquad \text{(formula 1)}$$

wherein $B^1$ is ttgg or ccaa and $B^2$ is correspondingly ccaa or ttgg and xN represents a sequence of from 1 to 30 intervening nucleotides, preferably 3 to 30 nucleotides, which is substantially native to the promoter region of the gene coding for a cytokine, said intervening nucleotides being the same or different and optionally comprising (i.e. consisting of or including) palindromic sequence, together with the complementary strand, the oligomer being modified to make it resistant to degradation and denaturing in vivo. Preferably the oligomer is terminated by stability-imparting c or g nucleotides at each end. It can be made degradation-resistant in any of the known ways, especially by replacing 50–100% of phosphate bonds therein by phosphorothiorates. An alternative method is to clone the oligomer(s) into a plasmid.

The invention is not necessarily applicable to every single cytokine, but only to those which have the required sequence of formula (1). As will be seen later, this includes most of the best known human cytokines, especially those which are produced by T-helper (Th) cells. However, it also applies to certain other cytokines, such as those produced by macrophages.

Generally stated, the cytokines to which the present invention applies can easily be determined by searching for a palindrome-containing sequence of formula (1). Within the promoter region, or if the promoter region is not yet identified, it should be regarded as the first 3000 bases, especially the first 1000 bases, of 5'-non-coding region preceding the coding region, i.e. upstream of ATG. By definition, the promoter region is also upstream of the start site for transcription of RNA, and therefore that part of the 5'-non-coding region which is transcribed to mRNA or is an intron of the gene is excluded. Extensive lengths of promoter sequence have been published for many cytokines, so sequencing will rarely be necessary.

As mentioned earlier, the invention also includes a vector containing at least one copy of a ds-DNA palindrome sequence (one strand only shown) of formula (1) above, together with the complementary strand. The vector may be for example a plasmid or a phage or a modified viral vector. This approach has the advantage of permitting multiple copies of the DNA sequence, e.g. up to 100, to be administered and provides more stability in the form of a circular plasmid/vector.

The invention also includes pharmaceutical formulations of the above-defined DNA or vector, especially liposomes containing the DNA or vector.

Also within the invention is the medical use of the above DNA, expressed in any way permitted by patent law. Thus, in the United States and Australia it includes a method of treating a disease associated with over-production of a cytokine especially by over-expression of the gene, the method comprising the administration to a patient in need thereof of an effective amount of the DNA oligomer, vector or pharmaceutical formulation as defined above. For Europe and those countries which adopt European Patent Convention or similar law, it includes the DNA, vector and pharmaceutical formulation, for use in the therapy of the said disease and the use of the DNA or vector in the preparation of a pharmaceutical formulation for that purpose.

DESCRIPTION OF THE PREFERRED EMBODIMENTS

The ds DNA oligomer of the invention inhibits the production of cytokine(s) in human cells. It is hypothesised that it is competing with the native cytokine genomic DNA for a putative transcription factor. The transcription factor is "putative" because it has not so far been identified or isolated but it is not necessary to do so for the purposes of the present invention. The invention is not dependent on the correctness of this hypothesis. What matters is that the approach of the present invention will inhibit the cytokine. Moreover, specifically in relation to hIL-5, the oligomer tested, described below, has relatively little effect on hIL-2 and hIFN-γ. Likewise, in relation to TNF-α, the oligomer tested, described below has little or no effect on hIL-2, hIL-5 and hIFN-γ.

The xN part of the palindrome-containing sequence may have from 1 to 30 nucleotides and is termed herein "the xN sequence", notwithstanding that, strictly, one nucleotide is not a sequence. The xN sequence will normally be exactly as it occurs in the 5'-NCR of a cytokine. If there are allelic variations in the natural sequence, then any allele of the xN sequence can be selected, preferably having regard to the properties of the expressed cytokine associated with that allele, as seems medically appropriate. In any event, the xN sequence can be modified from the native sequence provided that the modification does not affect the ability of the oligomer or vector to compete with the native sequence. Thus, the xN sequence can be varied by deletion, addition or substitution of (say) 1 to 3 base pairs from a native sequence, although the length requirements of xN (1 to 30) still apply to the modification. "Substantially native" in this context should be construed liberally accordingly.

The length is somewhat arbitrarily selected but, on the basis that some degree of separation is required between the ttgg and ccaa portions, xN cannot be zero. As regards the upper limit, there must be a point at which the chain between these portions would fold so excessively as to make it improbable that the palidrome would function effectively. This is judged to be 30 nt, although it is not out of the question that the effects might be obtained at longer lengths.

Preferably, the ds DNA oligomer of the invention is stabilised against cleavage to ss DNA by making its ends rich in g-c bonds between the two strands. In practice, this means that at least the terminal nucleotide and usually its neighbour are g or c and this applies at both the 5' and 3' ends. Preferably a g-c rich end (either or both ends) consists of two or more g-c base pairs per end, e.g. from 2 to 4 bp.

Where the ends of the oligomer have g-c rich ends, the next adjacent nucleotides can be those of the 5'- or 3'- end respectively of the palindrome-containing sequence, i.e. $B^1$ or $B^2$ of formula (1). Alternatively, any arbitrary flanking nucleotides (not interfering with base-pairing between $B^1$ and $B^2$) can precede $B^1$ or follow $B^2$, respectively, between $B^1$, $B^2$ and the ends.

readily be found by simple trial and error, using an ELISA with a monoclonal antibody, to check for inhibition of cytokine production. The term "substantially native" should be construed liberally accordingly. Taking IL-S as an example, given that the total length of the oligomer is most preferably 25 to 60 bp, that the preferred g-c ends are typically 5 bp long in total, and that the palindrome-containing sequence is 11 bp long, the total flanking sequence is typically from 9 to 44 bp and it may be disposed substantially symmetrically about the palindrome or asymmetrically. Thus, the length of outward flanking sequence on each side of the palindrome is not necessarily the same. For example, the 5'-flanking sequence can be longer or shorter than the 3'-flanking sequence. Preferably the outward flanking sequences are between 5 and 10 bp each side, thus permitting one or two deletions or variations on each side. As explained below, the native flanking sequence sometimes extends the palindrome sequences outwardly, i.e. these nucleotides are palindromic themselves.

Tables 1 and 2 show some examples of palindrome-containing sequences conforming to formula (1) above.

TABLE 1

| SEQ ID NO: | Cytokine | Palindrome-containing sequence fitting general formula (1) | Ref: | Nucleotide Nos. from Start Codon |
|---|---|---|---|---|
| 1 | hIL-2 | ttgg .... (14N) .... ccaa | A | −220 to −199 |
| 2 | hIL-4 | ccaa .... (14N) .... ttgg | B | −498 to −477 |
| 3 | hIL-5 | ccaa .... (3N) .... ttgg | C | −514 to −504 |
| 4 | hIL-6 | ttgg .... (17N) .... ccaa | D | −796 to −771 |
| 5 | hIL-8 | ccaa .... (8N) .... ttgg | E | −533 to −518 |
| 6 | hIL-8 | ttgg .... (21N) .... ccaa |  | −1310 to −1282 |
| 7 | hIL-10 | ttgg .... (24N) .... ccaa | F | −484 to −453 |
| 8 | hIL-10 | ccaa .... (19N) .... ttgg |  | −1148 to −1120 |
| 9 | hIL-13 | ttgg .... (24N) .... ccaa | G | −93 to −62 |
| 10 | hIL-13 | ccaa .... (26N) .... ttgg |  | −411 to −378 |
| 11 | hGM-CSF | ttgg .... (22N) .... ccaa | H | −314 to −285 |
| 12 | hTNF-α | ttgg .... (3N) .... ccaa | I | −865 to −875 |

References [and nucleotide numbering in the reference]
A. T. Fujita et al., Proc. Natl. Acad. Sci. USA 80, 7437–7441 (1983) [258 to 279].
B. N. Arai et al., J. Immunol. 42, 274–282 (1989) [673 to 694].
C. T. Tanabe et al., J. Biol. Chem. 262, 16580–16584 (1987) [39 to 49].
D. K. Yasukawa et al., EMBO J. 6, 2939–2945 (1987) [−796 to −771].
E. N. Mukaida et al. submitted to Genbank under Accession No. M28130 [274 to 302; 1051–1066] or J. Immunol. 143, 1366–1371 (1989)
F. J. S. Rumbyrt et al., submitted to Genbank under Accession No. HSU06844 [913 to 941]; D. Kube et al., Immunogenetics 45, 82–83 (1996).
G. A. N. J. McKenzie et al., J. Immunol. 150, 5436–5444 (1993) [679 to 710; 361 to 394].
H. S. Miyatake et al., EMBO J. 4, 2561–2568 (1985) [439 to 468].
I. S. Takashiba et al., Gene 131, 307–308 (1993) [−698 to 696], D. Pennica et al., 312, 724–729 (1984) [shows ATG start codon at 796–798].

Preferably substantially native flanking nucleotides are used. "Native" means of the same sequence as in the cytokine gene 5'-non-coding region from which the palindrome-containing sequence is derived. Either $B^1$ or $B^2$ or both can be thus flanked. "Substantially native" in this context indicates that some modification is possible in the native sequence, e.g. by deleting, varying, or adding (say) 1 to 3 base pairs. The degree of possible modification can Whether the oligomer is used as such or the palindrome containing sequence is carried within a vector such as a plasmid containing one or more copies of its DNA sequence, the relevant DNA can be given to the patient by any known method for cellular therapy in which DNA is introduced into cells. This may include, containing the relevant DNA, transfection by retroviral vectors, and conjugation with cholesterol.

TABLE 2

| SEQ ID NO: | Cytokine | Complete palindrome-containing sequence | | | | Length |
|---|---|---|---|---|---|---|
| 1 | hIL-2 | ttggggttt | aaagaattcc | aa | | 22 |
| 2 | hIL-4 | ccaagatgcc | acctgtactt | gg | | 22 |
| 3 | hIL-5 | ccaaggcttg | g | | | 11 |
| 4 | hIL-6 | ttgggagacg | gcaggcagca | gccaa | | 25 |
| 5 | hIL-8 | ccaataaaat | gattgg | | | 16 |
| 6 | hIL-8 | ttggtgtgct | ctttatctac | agaatccaa | | 29 |
| 7 | hIL-10 | ttgggtattc | atcccaggtt | gggggaccc | aa | 32 |
| 8 | hIL-10 | ccaagacaac | actactaagg | cttctttgg | | 29 |
| 9 | hIL-13 | ttgggcctat | aaaagctgcc | acaagagccc | aa | 32 |
| 10 | hIL-13 | ccaaaagggt | ctgaggacag | gagctcagag | ttgg | 34 |
| 011 | hGM-CSF | ttggaaaggt | tcattaatga | aaaccccccaa | | 30 |
| 12 | hFNF-α | ttggaagcca | a | | | 11 |

The intervening nucleotide sequence between ttgg and ccaa can contain palindromic nucleotides. These can form an independent inner palindrome, as in hGMCSF or hIL-2 (which has a palindrome tttaaa in the middle) or they can extend the existing palindrome inwards. For example, the following cytokine promoter sequences form inwardly extended palindromes in this way:

| h IL-4 | ccaag | .... | 12N | .... | cttgg |
| h IL-5 | ccaag | .... | 1N | .... | cttgg |
| h IL-10 | ttggg | .... | 22N | .... | cccaa |
| h IL-10 | ccaag | .... | 19N | .... | tttgg |
| h IL-13 | ttgggc | .... | 24N | .... | gcccaa |

For the purposes of clear definition any nucleotides, palindromic or not, inwards of the ttgg and ccaa are considered part of the 1 to 30 intervening nucleotides represented by xN in formula (1).

In other instances, natural flanking sequence also forms an outwardly extended palindrome, for example:

| h IL-2 | tctttgg | .... | 14N | .... | ccaaaga |
| h IL-4 | ttccaag | .... | 12N | .... | cttggaa |
| h IL-8 | cttgg | .... | 21N | .... | ccaag |

The oligonucleotides of the invention can be structured to include at least one pair of nucleotides flanking nucleotides ttgg or ccaa at either or both ends, thereby extending the palindrome to comprise 5 or more pairs of nucleotides. (Note: the term "pair of nucleotides" means a palindrome-forming pair within a single strand of DNA and should not be confused with base pairs.) Indeed, most of the above-exemplified cytokines have palindrome-containing sequences conforming to the preferred general formula (2):

$$5'N^1\text{-}B^1\text{-}N^3\text{-}yN\text{-}N^4\text{-}B^2\text{-}N^2 3' \quad (2)$$

wherein either the pair $N^1$ and $N^2$ or the pair $N^3$ and $N^4$ or both these pairs are palindromic nucleotides and yN represents 1–28 nucleotides of the native cytokine gene sequence in the 5' non-coding region, $B^1$ and $B^2$ being as defined in formula (1). Such palindrome-containing sequences are a preferred sub-genus of formula (1).

The oligonucleotides can be modified in any known way to make them less liable to degradation in vivo. Preferably they are phosphorothioated. The degree of phosphorothioate linkage is not critical but will normally be between 50 and 100%, preferably between 70 and 80%, based on the total number of phosphate bonds.

In the present invention it has been found necessary to use an oligomer which is relatively long. This length refers to the whole oligomer, not just the palindrome-containing sequence. Shorter oligomers of IL-5 promoter sequence of lengths 17 and 23 bp were prepared and tested, but found unsuccessful. A preferred length is 25 to 50 bp and 27 to 45 bp is most preferred.

A preferred oligomer of the invention for use in inhibiting IL-5 is designated "R27" and has the 27 bp long sequence (SEQ ID NO:13) cgaccctgcc aaggcttggc agttggc. 27

A preferred oligomer of the invention for use in inhibiting TNF-α is designated "R42" and has the 42 bp long sequence (SEQ ID NO: 14) cagggaccc agagttcctt ggaagccaag actgaaacca gc, palindrome being underlined.

SEQ ID NO: 13 and 14 are "artificial" for the purposes of Sequence Listing and contain free text under identifier <223>, as follows:
SEQ ID NO: 13 "Oligomer containing palindromic sequence from human IL-5 promoter" and
SEQ ID NO: 14: "Oligomer containing palindromic sequence from human TNF-alpha promoter".

Figure 3:
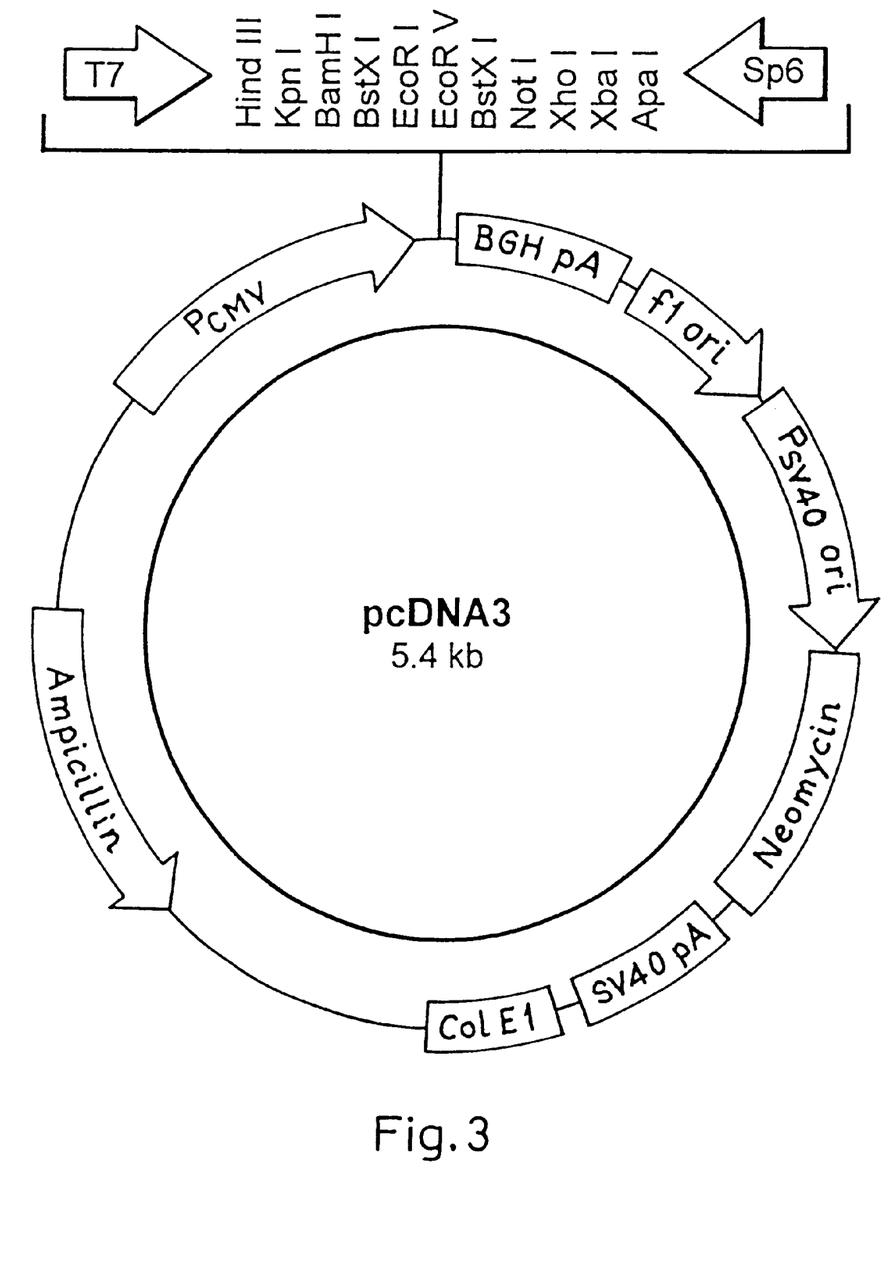
FIG. 3 is a diagram of the pcDNA3 plasmid taken from the web site of Invitrogen, Inc.

The oligomer could be used as naked DNA, but to synthesise oligomer, even using the PCR, is relatively expensive and a big quantity is needed to achieve effective inhibition by competition. Therefore, an alternative way is to insert palindrome-containing sequence, either as such or as the oligomer in a multi-copy plasmid, preferably a bacterial plasmid, so that it can be multiplied in the usual way by bacterial fermentation methods, whereby each cell contains a high number of copies of the plasmid. Further, each plasmid can contain more than one copy of the palindrome-containing sequence, or one or more copies of different palindrome-containing sequences, derived from promoters of the same or different cytokines. The above-mentioned plasmids are preferably used as the inhibitor DNA. Plasmids suitable for adding inserts are well known and commercially available from many commercial companies, such as Promega or Invitrogen. For instance, pcDNA3 from Invitrogen, Inc can be used. For the structure of this plasmid, see web page www.invitrogen.com/vecgif/pcdna3.dif. It contains, in order, a CMV promoter, followed by the T7 promoter, a polylinker providing a multiple cloning site and an sp6 promoter for transcription in the reverse direction to the T7 promoter. A diagram is provided in FIG. 3.

The g-c-rich ends, highly desirable in the oligomer, are not necessarily desirable if the oligomeric sequence is inserted into a vector, since the vector will normally prevent the DNA from unwinding into single strands. Also, when using a vector, the nucleotides or phosphate bonds need not be modified for resistance to degradation. In other words, the oligomer is made resistant to denaturing and degradation by introducing it into the vector and the term "oligomeric sequence" used herein in this context should be construed accordingly. When a vector is used, the oligomeric sequence could be longer than 150 bp, e.g. say up to 200 bp, since it is more stable when present in the vector. However, since the sequence outwards of the palindrome is not necessarily native to the cytokine gene, it follows that it will not always be possible or meaningful to distinguish the exact length of the oligomeric insert in the plasmid. Indeed, the insert in the vector may be of the palindrome-containing sequence above, without there necessarily being any of the outwardly flanking nucleotides present in the oligomer.

Whether the oligomer is used as such or the palindrome-containing sequence is carried within a vector such as a plasmid containing one or more copies of its DNA sequence, the relevant DNA can be given to the patient by any known method for cellular therapy in which DNA is introduced into cells. This may include, for example, encapsulation in drug delivery vehicles, e.g. a liposome formulation, containing the relevant DNA, transfection by retroviral vectors, and conjugation with cholesterol.

Drug delivery vehicles are effective for both systematic and topical administration. They can be designed to serve as a slow release reservoir, or to deliver their contents directly to the target cell. Some examples of such specialised drug delivery vehicles are liposomes, hydrogels, cyclodextrins, biodegradable nanocapsules, and bioadhesive microspheres.

Liposomes are preferred. They are hollow spherical vesicles composed of lipids arranged in a similar fashion as the lipids of the cell membrane. They have an internal aqueous space for entrapping water soluble compounds and range in size from 0.05 to several microns in diameter. Liposomes can deliver the DNA to cells, so that the nucleic acid remains biologically active. They can easily be prepared by mixing the DNA with a liposome-forming lipid such as a dialkyl or diacylglycerol or phosphatidinylcholine, as known in the art of liposome formation. See J. J. Rossi et al. AIDS Research and Human Retroviruses 8, 183–189 (1992).

Liposome preparations useful in the invention comprise: (a) lipofectamine reagent (GIBCO BRL, Gaithersburg, Md. USA) containing a polycationic lipid molar ratio, (b), the cationic lipid, DDAB and DOPE, in a 2:1 ratio, R. Philip et al. Mol. Cell. Biol. 14, 2411–2418 (1994); and (c) DMRIE, optionally in combination with DOPE, e.g. in a 1:1 molar ratio (VICAL Corp. San Diego, Calif., USA). Newer liposomes, for example the serum-resistant cationic lipid GS 2888, J. G. Lewis et al., Proc. Natl. Acad. Sci. USA 93, 3176–3181 (1996) and liposomes containing a polylysine/DNA complex, S. Li and L. Huang, J. Liposome Research 7, 63–75 (1997), can also be used.

Nanoparticles and hydrogel carriers have been developed for chemotherapeutic agents and protein-based pharmaceuticals, and consequently, can be adapted for delivery of the DNA for the purposes of the present invention.

Another delivery method is via white cells. Compatible white cells, preferably the patient's own, are transfected with DNA of the invention, for example by electroporation and the patient is then infused with these cells. Electroporation of such cells (lymphocytes) with DNA is described in Example 6 of PCT Publication WO 96/22638 (Gene Shears Pty Ltd.) and this method can be applied in the present invention.

The invention can be used in any form of therapy in which it is desired to suppress, reduce or alleviate the patient's production of the relevant cytokine, especially when the patient is producing an abnormal concentration of the cytokine in his body cells. Preferably the invention is applicable to human diseases and human cytokines. The relevant cytokine includes any of the human interleukins. Diseases associated with excess cytokine production, or treatable by inhibiting cytokine production, are well known. For example, IL-5 is over-produced by asthmatic patients. IL-6 induces the production of acute phase proteins including C-reactive protein. This action of IL-6 has been cited playing a role in angina [L. M. Biasucci et al., Circulation 94, 874–877 (1996)] and pancreatic cancer [S. Okada et al., Japanese Journal of Clinical Oncology 28, 12–15 (1998)]. PCT Application Publication No. WO 98/36061 (Manchester University) relates to the reduction of fibrosis or wound scarring by inhibiting IL-6 and the present invention can also be used for this purpose. Excess IL-4 and IL-13 can lead to production of IgE and hence allergic symptoms. IL-10 has been implicated in post-operative immunosuppresion, through reducing expression of MHCII from monocytes [(A. Klava, Archives of Surgery 132, 425–429 (1997)]. IL-10 also has many effects on other cytokines, e.g. as an inhibitor of IL-8 and inhibits the proliferation of human peripheral blood T-cells: see e.g. PCT Patent Application Publication WO 96/01318 (Nycomed Dak A/S) pages 6 and 7. TNF-α can cause septic shock syndrome and cancer cachexia and play a crucial part in inflammatory diseases such as rheumatoid arthritis. IL-15, a T-cell growth factor, can cause excessive cellular proliferation.

Dosages of the DNA of the present invention can vary between wide limits, depending upon the disease or disorder to be treated, the age and condition of the individual to be treated, the severity of the illness, etc and a physician will ultimately determine the appropriate dosages to be used. This dosage may be repeated as often as appropriate. If side effects develop the amount and/or frequency of the dosage can be reduced, in accordance with normal clinical practice.

The following Examples illustrate the invention.

EXAMPLE 1

Inhibition of IL-5 release in Human Blood Peripheral Mononuclear Cells

The oligomer R27, modified to have a phosphorothioate content of about 70–80% (based on total number of phosphate groups in the unmodified oligomer) was synthesised using an oligosynthesizer. Equal amount of the two strands of DNA were mixed and boiled, then left at room temperature to anneal.

Using an ELISA to detect cytokine release, studies have been performed on human T-cell, clones and lines obtained from human blood peripheral mononuclear cells from normal individuals using anti-CD3 antibody every 7 days and IL-2 feeding every 3–4 days. T-cells were incubated with 5–10 μg/ml of R27 for 3 hours at 37° C. at the end of feeding cycle, i.e. 7 days after previous stimulation, with no extra IL-2 fed at day 3 or day 4. The cells were then incubated with anti-CD3 monoclonal antibody immobilised on plastic. (This antibody stimulates T-cells and IL-5 production.) The culture supernatants were collected 24 hours later. The ELISA used was of the calorimetric sandwich type, "Quantikine" (Registered Trade Mark) by R & D Systems, Inc, Minneapolis, USA, or R & D Systems Europe, Abingdon, Oxfordshire, England. A murine monoclonal capture antibody against the cytokine, coated on a microtitre plate, is provided. The detection antibody is a polyclonal antibody against the cytokine linked to horseradish peroxidase. The colour-forming reagents are hydrogen peroxide and tetremethylbenzidine. Optical density is read at 450 nm.

Figure 1A:
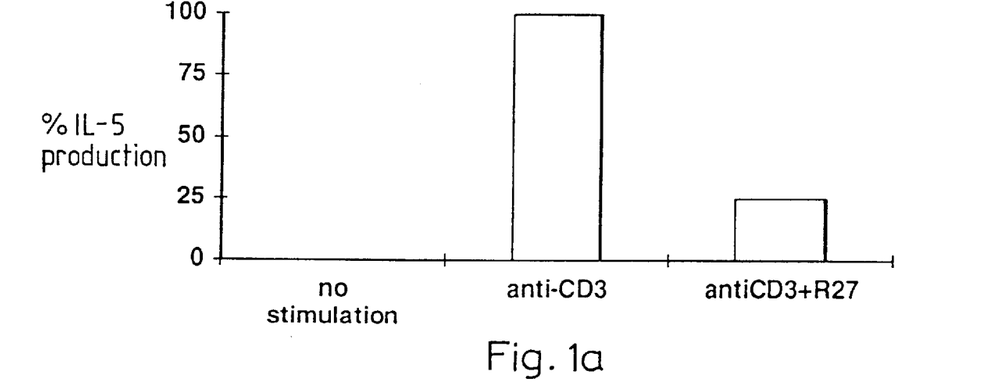
FIGS. 1a to 1c show the results of an assay for inhibition of IL-5 production using a palindrome-containing modified ds DNA oligomer "R27" of the invention in (1a) a human Th2-like T-cell clone to measure the remaining percentage of IL-5 production, (1b) a human Th2-like T-cell clone to measure the remaining percentage of IL-2 production, (1c) a human Th2-like T-cell line to measure the remaining percentage of IFNγ production.
Figure 1B:
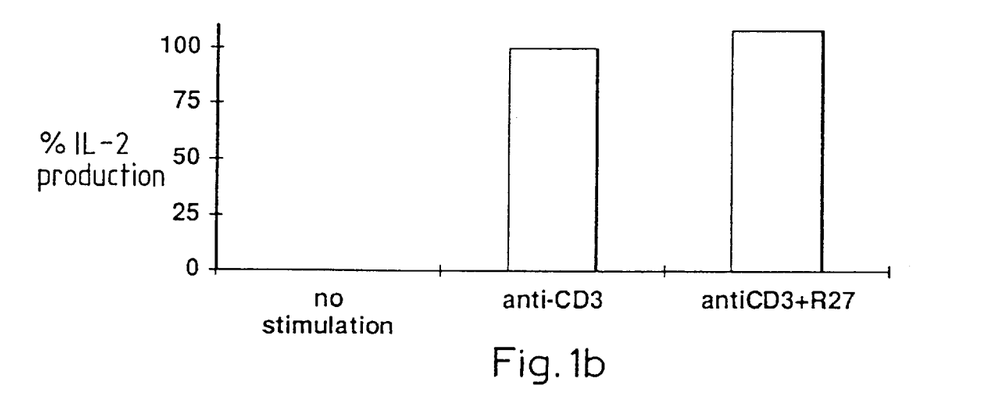
Figure 1C:
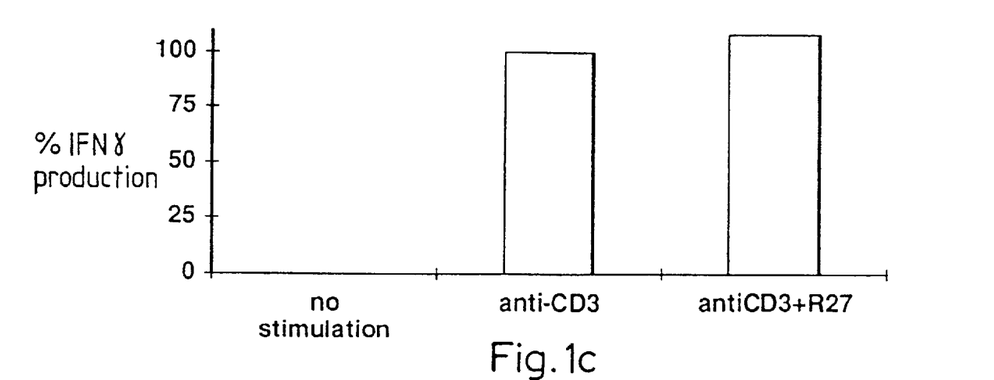

The results in FIG. 1a show that R27 was able to inhibit IL-5 production induced by stimulation with anti-CD3 molecules. As shown in FIGS. 1b and 1c, the production of other cytokines such as IL-2 and IFNγ was not affected. Culture protocols for T-cell culture were as described in Masseyeff et al. in Methods of Immunological Analysis 3, 121–138, VCH Verlag, Weinheim, Germany (1993).

Figure 2:
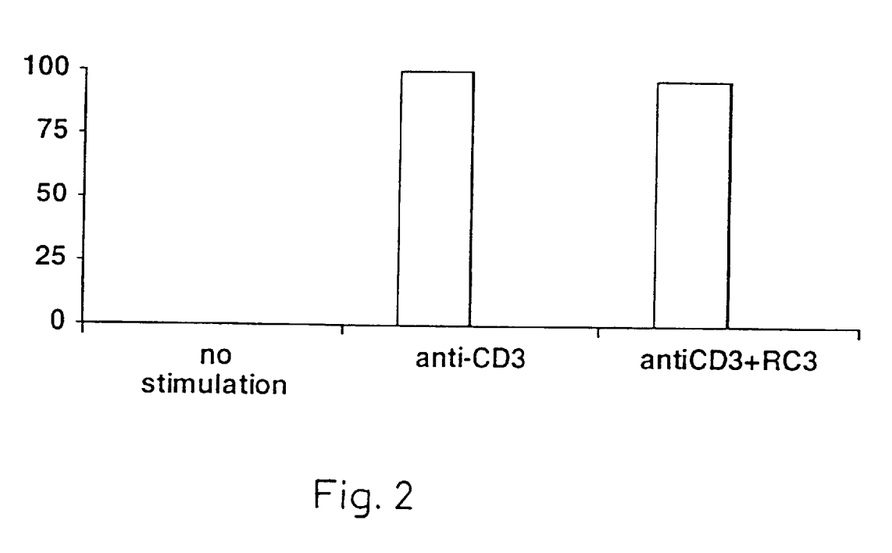
FIG. 2 shows the results of a control experiment to measure the percentage of remaining IL-5 production in a human Th2-like cell using a control modified ds DNA, not related to IL-5 gene, called "RC3"

Using a 27 bp ds DNA control oligomer "RC3":

gctgcctcgc cgtatgggtg atgacgg (SEQ ID NO: 15)

instead of R27, no inhibition of IL-5 production was obtained, as shown in FIG. 2. SEQ ID NO: 15 is "artificial" for the purposes of Sequence Listing and contains free text under identifier <223> as follows: "Oligomer of no known origin". It has g-c-rich ends and lacks the palindrome of SEQ ID NO: 13.

EXAMPLE 2

Inhibition of TNF-α Production in Human Blood Peripheral Mononuclear Cells

The oligomer sequence containing the palindrome (underlined) was selected as "R42"(SEQ ID NO: 14). Two primers were synthesised incorporating EcoRI site nucleotides aattc at the 5'-ends for cloning purposes. Thus the forward primer comprised aattc followed by SEQ ID NO: 14, while the reverse primer (read 5' to 3') comprised aattc followed by the complement of SEQ ID NO: 14.

The two oligos were hybridised together as described in Example 1. This was followed by digestion with EcoRI before ligation of the, now, double stranded DNA in the relevant ligation buffer. The ligated product was run on 1% agarose gel for separation and a heavy band (indicating a large molecular size) was cut out and purified by-dialysis ("Molecular Cloning: A Laboratory Manual" $2^{nd}$ ed. 1989, ed. Sambrook, Fritzsch and Maniatis, pages 6.28 and 6.29). Thus, the gel slice was inserted into a dialysis bag filled with electrophoresis buffer, the bag was closed and immersed in a shallow layer of the buffer in an electrophoresis tank. Current at 50V, 45 mA was passed through the bag for approximately 45 minutes, monitoring every 15 minutes. After reversing the polarity of the current for 1 minute to release DNA from the inner wall of the bag, the bag was removed from the tank and the buffer removed from the bag. The bag was washed out with the buffer and the washings collected. The buffer used was 1×TAE (Tris Acetate EDTA).

Cloning was performed by ligation of the ds oligo DNA into the pcDNA3 plasmid as described by the manufacturer, Invitrogen, Inc. The plasmid had been cut with EcoRI and dephosphorylated before the ligation. The procedure followed the instructions of manufacturer of pcDNA3. The plasmid (containing the oligo DNA) was tranfected into JM109 bacteria and the colonies were screened using PCR. The primers for this PCR were based on the T7 and Sp6 sites contained in the plasmid, which flank the polylinker (see FIG. 3). Positive clones were selected for further assays, the plasmids were digested with restriction enzymes and sequenced, confirming that the plasmid contained 2 copies of the selected gene sequence.

Figures 4, 5:
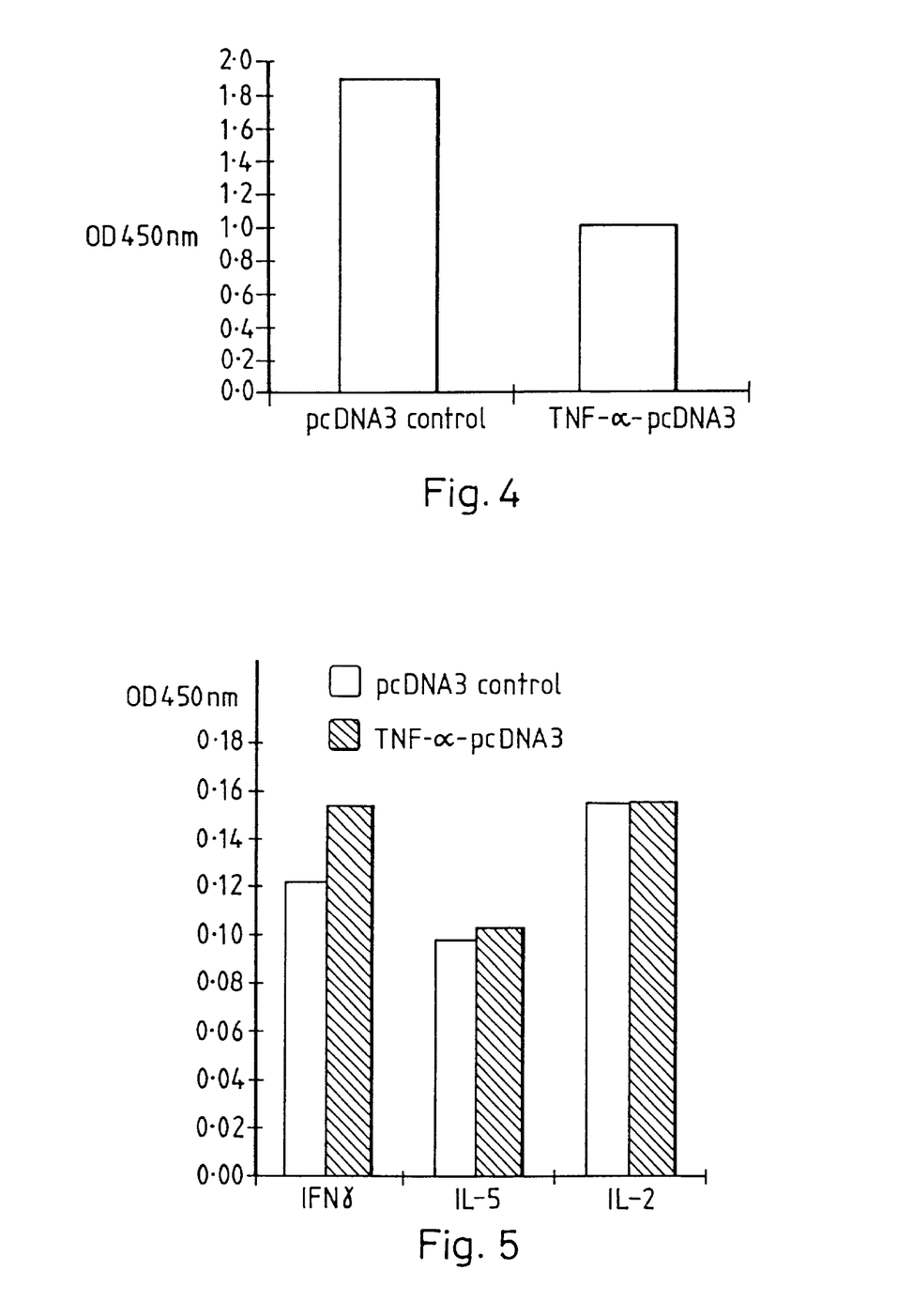
FIG. 4 shows assay results similar to those of FIG. 1(a), but in which TNF-α production is inhibited using a plasmid containing the sequence of a palindrome-containing oligomer of the invention.
FIG. 5 shows assay results for inhibition of TNF-α similar to those of FIGS. 1(b) and 1(c), but in which IL-5, IL-2 and IFN-γ production remain uninhibited.

Inhibition of TNF-α production was demonstrated as follows. Peripheral blood mononuclear cells were isolated as described by the manufacturer of DMRIE-C and transfection was carried out using DMRIE-C (Gibco, Life Technologies Ltd.) as described in Example 1. The cells were stimulated with PHA-L lectin at 1 μg/ml and 10 μ IL-2/ml in RPMI 1640 standard culture medium with 10% foetal calf serum. After overnight incubation at 37° C., culture supernatants were collected and ELISA was carried out as in Example 1. FIG. 4 shows the inhibition of TNF-α production and FIG. 5 shows that the inhibition was specific as it does not affect IFNγ, IL-5 and IL-2 production.

All the prior references cited herein for the purpose of referring to known materials, sequences and procedures are hereby expressly incorporated herein by reference to the extent of describing the materials, sequences and procedures referred to.

What is claimed is:

1. A vector containing nucleotide sequence from a cytokine gene, said cytokine being selected from human interleukins and human TNF-alpha, said nucleotide sequence consisting of one or more copies of a double stranded oligomeric DNA sequence which is a substantially native sequence of the promoter region of the cytokine gene, said oligomeric sequence consisting of a length of 9 to 200 base pairs and containing a palindromic sequence of formula (1):

$$5'B^1 \ldots xN \ldots B^2 3'$$

and its complementary strand, wherein $B^1$ and $B^2$ together form a palindrome, $B^1$ is a ttgg or ccaa sequence and $B^2$ is correspondingly a ccaa or ttgg sequence, said $B^1$ and $B^2$ sequences being the same as in said promoter region of said cytokine gene, and xN represents a sequence of from 1 to 30 intervening nucleotides which is substantially identical with the native promoter region of said cytokine gene.

2. The vector of claim 1 wherein the oligomeric sequence has a length of 9 to 150 base pairs.

3. The vector of claim 1 wherein the oligomer sequence has a length of 25 to 60 base pairs.

4. The vector of claim 1, wherein the cytokine is human IL-5.

5. The vector of claim 1, wherein the cytokine is human TNF-α.

6. A drug delivery vehicle containing a vector claimed in claim 1.

7. Liposomes containing a vector claimed in claim 1.

* * * * *

SEQUENCE LISTING

```
<160> NUMBER OF SEQ ID NOS:  15

<210> SEQ ID NO 1
<211> LENGTH: 22
<212> TYPE: DNA
<213> ORGANISM: Human interleukin-2 promoter

<400> SEQUENCE: 1
ttgggggttt aaagaattcc aa                                             22

<210> SEQ ID NO 2
<211> LENGTH: 22
<212> TYPE: DNA
<213> ORGANISM: Human interleukin-4 promoter

<400> SEQUENCE: 2
ccaagatgcc acctgtactt gg                                             22

<210> SEQ ID NO 3
<211> LENGTH: 11
<212> TYPE: DNA
```

```
<213> ORGANISM: Human interleukin-5 promoter

<400> SEQUENCE: 3
ccaaggcttg g                                                          11

<210> SEQ ID NO 4
<211> LENGTH: 25
<212> TYPE: DNA
<213> ORGANISM: Human interleukin-6 promoter

<400> SEQUENCE: 4
ttgggagacg gcaggcagca gccaa                                           25

<210> SEQ ID NO 5
<211> LENGTH: 16
<212> TYPE: DNA
<213> ORGANISM: Human interleukin-8 promoter

<400> SEQUENCE: 5
ccaataaaat gattgg                                                     16

<210> SEQ ID NO 6
<211> LENGTH: 29
<212> TYPE: DNA
<213> ORGANISM: Human interleukin-8 promoter

<400> SEQUENCE: 6
ttggtgtgct ctttatctac agaatccaa                                       29

<210> SEQ ID NO 7
<211> LENGTH: 32
<212> TYPE: DNA
<213> ORGANISM: Human interleukin-10 promoter

<400> SEQUENCE: 7
ttgggtattc atcccaggtt gggggaccc aa                                    32

<210> SEQ ID NO 8
<211> LENGTH: 29
<212> TYPE: DNA
<213> ORGANISM: Human interleukin-10 promoter

<400> SEQUENCE: 8
ccaagacaac actactaagg cttctttgg                                       29

<210> SEQ ID NO 9
<211> LENGTH: 32
<212> TYPE: DNA
<213> ORGANISM: Human interleukin-13 promoter

<400> SEQUENCE: 9
ttgggcctat aaaagctgcc acaagagccc aa                                   32

<210> SEQ ID NO 10
<211> LENGTH: 34
<212> TYPE: DNA
<213> ORGANISM: Human interleukin-13 promoter

<400> SEQUENCE: 10
ccaaaagggt ctgaggacag gagctcagag ttgg                                 34

<210> SEQ ID NO 11
<211> LENGTH: 30
```

```
<212> TYPE: DNA
<213> ORGANISM: Human GM-CSF promoter

<400> SEQUENCE: 11
ttggaaaggt tcattaatga aaacccccaa                                        30

<210> SEQ ID NO 12
<211> LENGTH: 11
<212> TYPE: DNA
<213> ORGANISM: Human tumour necrosis factor alpha promoter

<400> SEQUENCE: 12
ttggaagcca a                                                            11

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:  Oligomer
      containing palindromic sequence from human IL-5
      promoter

<400> SEQUENCE: 13
cgaccctgcc aaggcttggc agttggc                                           27

<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence: Oligomer
      containing palindromic sequence from human
      TNF-alpha promoter

<400> SEQUENCE: 14
cagggacccc agagttcctt ggaagccaag actgaaacca gc                          42

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Oligomer of
      no known origin

<400> SEQUENCE: 15
gctgcctcgc cgtatgggtg atgacgg                                           27
```